United States Patent

Dossel et al.

[19]

[11] Patent Number: 5,885,215

[45] Date of Patent: Mar. 23, 1999

[54] METHOD OF RECONSTRUCTING THE SPATIAL CURRENT DISTRIBUTION IN A BIOLOGICAL OBJECT, AND DEVICE FOR PERFORMING THE METHOD

[75] Inventors: Olaf Helmut Dossel, Tangstedt; Walter Heinrich Kullmann, Hamburg, both of Germany

[73] Assignee: U.S. Philips Corporation, New York, N.Y.

[21] Appl. No.: 543,600

[22] Filed: Jun. 25, 1990

[30] Foreign Application Priority Data

Jul. 6, 1989 [DE] Germany .............................. 3922150.4

[51] Int. Cl.[6] ................................................... A61B 5/05
[52] U.S. Cl. .......................................... 600/409; 324/248
[58] Field of Search ............................... 128/653 R, 731; 324/201, 248; 600/407, 409, 544

[56] References Cited

U.S. PATENT DOCUMENTS

| | | | |
|---|---|---|---|
| 4,390,840 | 6/1983 | Ganssen et al. | 324/309 |
| 4,736,751 | 4/1988 | Gevins et al. | 128/731 |
| 4,793,355 | 12/1988 | Crum et al. | 324/248 |
| 4,862,359 | 8/1989 | Trivedi et al. | 128/731 |
| 4,913,152 | 4/1990 | Ko et al. | 128/653 R |
| 4,940,058 | 7/1990 | Taff et al. | 128/653 R |

FOREIGN PATENT DOCUMENTS

| | | | |
|---|---|---|---|
| 3725532 | 2/1989 | Germany | A61B 5/04 |
| 3735668 | 5/1989 | Germany . | |

OTHER PUBLICATIONS

B. Jeffs, R. Leahy & M. Singie, "An Evaluation of Methods for Nouromanetic Image Reconstruction", IEEE Transaction on Biomedical Engineering, vol. BME–34,–No. 9, Sep. 1987, pp. 713–723.

V.O. Dossel & W. Kullmann, "Squids und Bilder Neuronaler Strome", Phys. B1., 44, (1988) NR. 11, pp. 423–425.

M, Hoke, "Squid–Based Measuring Techniques—A Challenge For The Functional Diagnostics in Medicine", The Art of Measurement: Metrology in Fundamental & Applied Physics, pp. 287–335, 1st Edition: 1988.

W.J. Dallas, W.E. Smith, H.A. Sclitt, & W. Kullman, "Bioelectric Current Image Reconstruction From Measurement of The Generated Magnetic Fields", Medical Imaging, SPIE, vol. 767, (1987), pp. 1–10.

S. Ueno et al., "The MEG Topography and The Source Model of Abnormal Neural Activities Associated with Brain Lesions", IEEE Transactions on Magnetics, vol. Mag–22, No. 5, Sep. 1986, pp. 874–876.

*Primary Examiner*—Brian Casler
*Attorney, Agent, or Firm*—Jack D. Slobod

[57] ABSTRACT

A method of reconstructing the spatial current distribution in a biological object, at least one component of the magnetic field produced by the current sources being measured at a number of points outside the object, after which the current distribution at the volume elements situated within the object is reconstructed from the measuring values. In order to improve the accuracy of reconstruction, in a representation containing the morphological structure of the object the surfaces are specified on which the current sources are presumably present, the reconstruction being limited to the volume elements which are situated on these surfaces.

2 Claims, 2 Drawing Sheets

METHOD OF RECONSTRUCTING THE SPATIAL CURRENT DISTRIBUTION IN A BIOLOGICAL OBJECT, AND DEVICE FOR PERFORMING THE METHOD

BACKGROUND OF THE INVENTION

1. Field of the Invention

The invention relates to a method of reconstructing the spatial current distribution in a biological object, at least one component of the magnetic field produced by the current sources being measured at a number of points outside the object, after which the current distribution at the volume elements situated within the object is reconstructed on the basis of the measuring values, and also relates to a device for performing the method.

A method and a device of this kind are known from the publication "SQUIDs und Bilder neuronaler Ströme" by O.Dössel and W. Kullmann (Phys. B1. 44 (1988) No. 11, pp. 423–425).

2. Description of the Prior Art

Therein, for the reconstruction, the magnitude and direction of the current densities in the individual volume elements constituting the three-dimensional object region must be calculated from the magnetic fields measured outside the object region to be examined. It can be demonstrated that this so-called inverse three-dimensional problem cannot be unambiguously solved. The known method, therefore, uses reconstruction algorithms which enable an approximative calculation of the current distribution. The distribution thus determined, however, deviates from the actual distribution.

It is to be noted that from the publication by J. W. H. Meijs et al. "The EEG and MEG, using a model of eccentric spheres to describe the head", IEEE Trans. Biomed. Eng., Vol. BME-34, pp. 913–920, 1987, it is already known to derive information regarding the individual head or brain geometry from magnetic resonance tomogram or computer tomograms, thus enabling more accurate determination of the position of a single current dipole. This known method aims to determine, using the values of the magnetic flux density measured at different measuring points, the position of a single tangential, point shaped current dipole in a volume conductor, i.e. so that the measured magnetic field corresponds as well as possible to the magnetic field which would be measured if the current dipole were present at the relevant area. This approach utilises magnetic resonance tomograms or computer tomograms which represent the morphology of the head and in which areas of similar electrical conductivity are marked so as to enable more accurate modelling of the volume currents in the brain.

It is an object of the present invention to provide a method of the kind set forth so that such deviations are reduced. This object is achieved in accordance with the invention in that in a representation which contains the morphological structure of the object the surfaces on which the current sources are presumably present are specified, the reconstruction being limited to the volume elements which are situated on the surfaces.

The invention is based on the recognition of the fact that for many brain activities it is known that the neuronal current sources are situated on given surfaces. For example, tumors can initiate epileptic attacks because of their space requirements. The interior of the tumor is electrically inactive, the epileptical focus (current source) is situated somewhere on the periphery of the tumor. For some forms of focal epilepsy which cannot be traced to a tumor, a morphologically modified region occurs; the focus pursued is very probably present on the periphery thereof. Finally, it is known that evoked fields which can be measured on the head after a stimulation of the sense organs originate from a spatially definable zone of the folded cerebral cortex.

Consequently, the reconstruction of the current source density takes place only for the specified (two dimensional) surfaces and not for a three dimensional region within the object to be examined. Consequently, the two dimensional inverse problem occurs which can in principle be unambiguously solved. Therefore, the reconstruction in practice is influenced merely by the fact that the measurement of the magnetic field is performed at a finite number of points and that measurement thus takes place with a finite accuracy.

A device for performing the method in accordance with the invention is characterized in that it comprises a measuring device for determining the magnetic flux density outside the object, a memory for storing the measuring values thus obtained, a unit for determining the volume elements which are situated on surfaces to be specified, and a reconstruction unit for determining the current distribution the volume elements from the values stored.

IN THE DRAWING

The invention will be described in detail hereinafter with reference to the drawing. Therein:

DESCRIPTION OF THE PREFERRED EMBODIMENT

Figure 1:
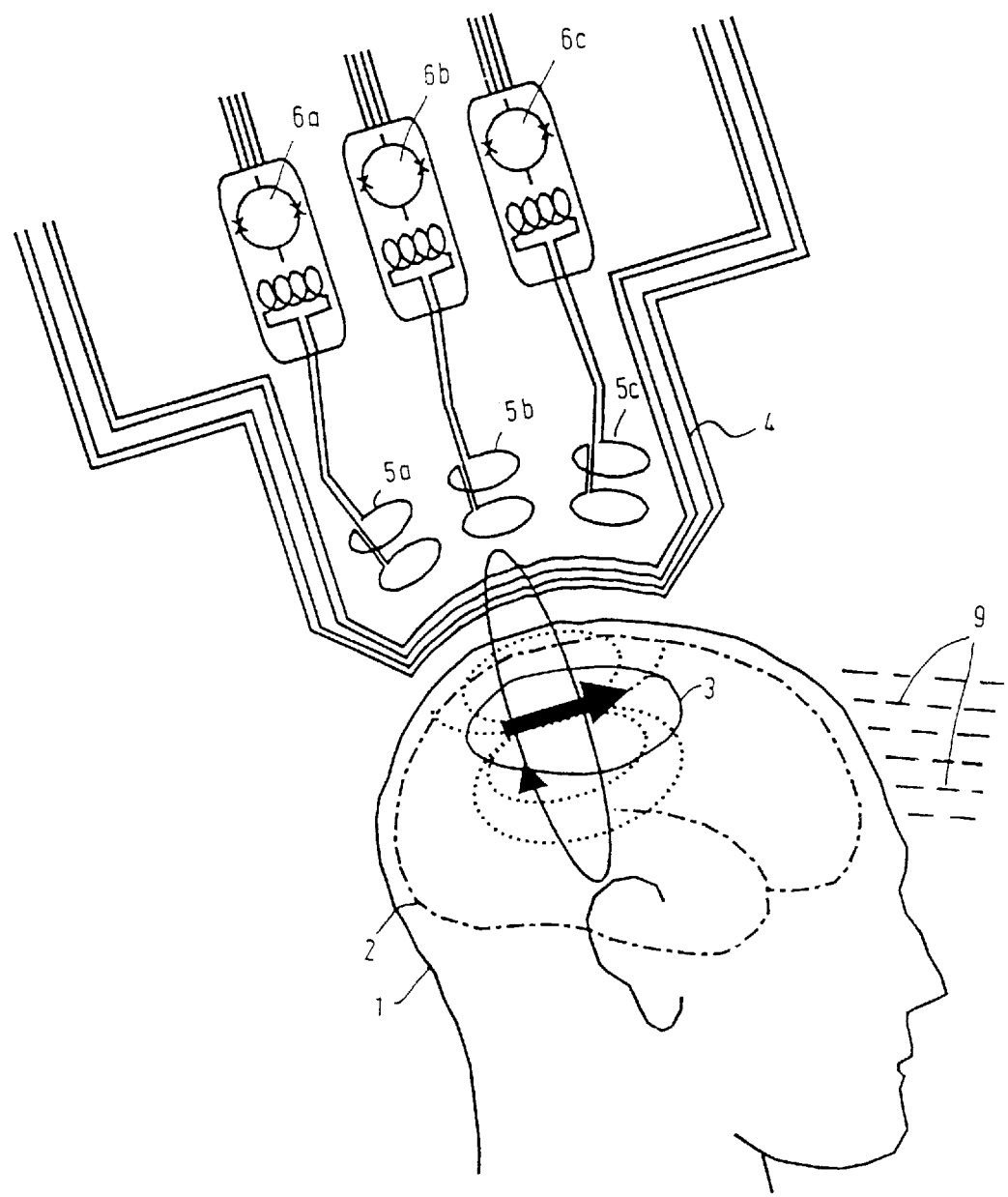
FIG. 1 shows a device for measuring the magnetic fields.

The reference numeral 1 in FIG. 1 denotes the skull of a patient and the reference numeral 2 denotes, by way of dash-dotted lines, the brain therein. The reference numeral 3 denotes the surface of a structure inside the brain which morphologically deviates from its environment, for example a tumor. It is also assumed that an impressed current, caused by electrochemical transformation processes, flows at the interface between the tumor and the healthy tissue, i.e. on its surface, the current being represented by a heavy arrow. Due to this impressed current, volume currents flow (dotted lines). These volume currents would not cause a magnetic field outside the skull should it be possible to consider the head to be an exactly spherical conductor.

Therefore, the radial component of the magnetic field measured outside the skull depends mainly on the impressed current, that is to say on the tangential component thereof. The current density of the tangential components of the impressed currents is to be determined as a function of location by measurement of the radial component of the magnetic field at a plurality of points outside the skull. More than one impressed current can thus also be localized and the current dipole need not necessarily be point-shaped.

For measurement of the radial component of the magnetic flux density there is provided, accommodated within a helium cryostat 4 arranged over the skull of the patient, a measuring system which comprises a plurality of measuring channels, each of which comprises a superconducting gradiometer (5a . . . 5c) which couples the magnetic flux density produced by the impressed current into a respective SQUID (6a . . . 6c). Measuring systems of this kind are known (DE-OS 37 35 668).

The present embodiment involves a measuring system comprising only three measuring channels, so that the magnetic flux density can be determined at three measuring points only. In practice, however, the magnetic field should be measured at more than three measuring points, for example at 19 or even more points. Therefore, a measuring system comprising a larger number of channels is required. However, for the measurement of evoked fields which can be measured after stimulation of the sense organs, use can also be made of a measuring system comprising only one measuring channel if such a measuring system is successively moved to a series of defined positions with respect to the skull. In each of these positions the variation in time of the magnetic field is then measured, the reference instant always being the instant at which stimulation takes place. Suitable measuring methods for the simultaneous or consecutive measurement of the magnetic field at different points are described in the article by M. Hoke "SQUID-Based Measuring Techniques" in "The art of Measuremento" Ed. by B. Kramer, VCH Verlagsgesellschaft mbH, Weinheim, 1988.

Figure 2:
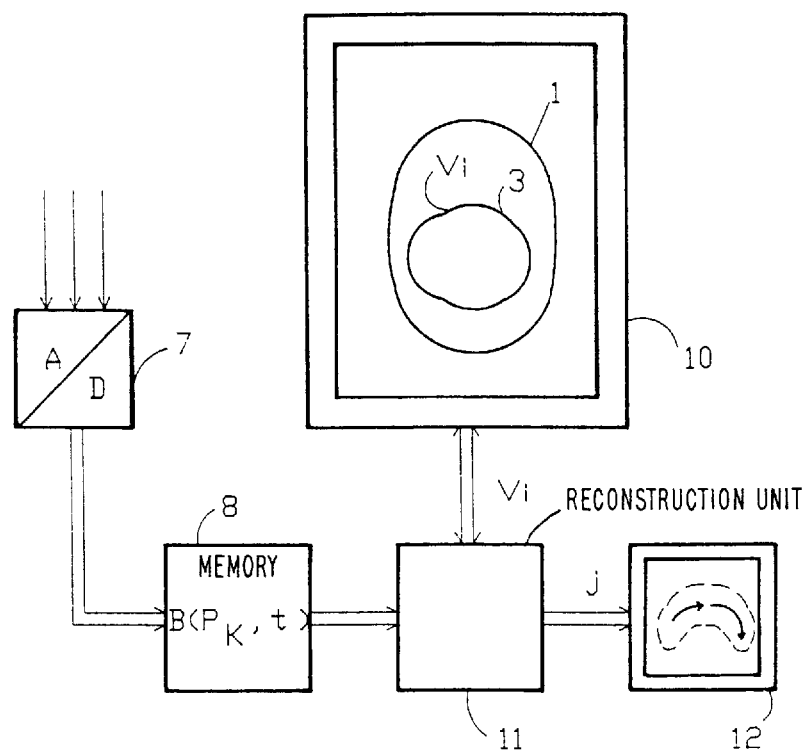
FIG. 2 shows a circuit diagram of a unit for processing the signals measured.

The analog measuring signals supplied by the individual measuring channels and representing the variation in time of the radial component of the magnetic flux density are applied to an analog-to-digital converter device 7 in which they are converted into a respective series of digital data words (FIG. 2). These data words are stored in a memory 8, after multiple repetition of the measurement and formation of the mean value which may be necessary for the measurement of the comparatively weak evoked fields in order to improve the signal-to-noise ratio (the control unit required for controlling the measuring channels and the units 7 and 8 has been omitted in FIG. 2 for the sake of simplicity). At the end of the measurement, the memory thus contains a set of digital values which represent the variation in time of the radial component B of the magnetic flux density for each measuring point $P_k$ (where k=1 . . . m) and m is the number of measuring points).

Before or after the measurement of the magnetic field the morphological structure of the skull or the brain is determined. This can be realized by way of an X-ray computer tomography device which forms computer tomograms of equidistant parallel slices through the skull of the patient as denoted by a set of parallel broken lines 9 in FIG. 1. The morphology can instead be determined by way of a magnetic resonance examination, in which case several (two-dimensional) magnetic resonance tomograms of parallel slice can again be formed; however, a three-dimensional imaging method can alternatively be used from the start. The morphology, however, can also be determined in a different way, for example using the so-called X-ray tomosynthesis.

As has already been explained, on the basis of the morphology of the skull it can in many cases be indicated from which surfaces of the brain the electrical activities thereof originate. This holds good for evoked currents which occur due to stimulation of the sense organs as well as for currents which occur spontaneously, for example in the case of an epileptical attack. These surfaces are specified by means of a unit 10, for example an interactive display which is used by the operator in order to mark the surfaces on which the centers of electrical activity are presumably situated. To this end, the slice images are successively displayed on the unit 10 and the relevant surfaces are suitably marked by the user, for example by means of a so-called light pencil. However, it is alternatively possible to determine the surfaces in an automatic unit 10 by means of a suitable contour searching algorithm which automatically determines the position of, for example a tumor. The unit 10 thus supplies the coordinates of the volume elements (voxels) $V_i$ which are situated on the desired surface which is denoted by the reference numeral 3 in the present case. These coordinates are suitably adapted to those of the magnetic field measuring system, for example by providing reference markers on the skull 1.

A reconstruction unit 11 reconstructs the density of the impressed current at the individual voxels $V_i$ (1 . . . i . . . s, where s is the number of voxels on the marked surface) from the measuring values of the magnetic flux density at the various pixels at each time the same instant. Known algorithms can be used for this purpose.

The relationship between the measuring values of the magnetic flux density B at the measuring points $P_k$ and the current density J at the voxels $V_i$ can be described in matrix form by a way of the Biot-Savart equation: B=A*j+n.

Therein, B is a column matrix of the type (m, 1), i.e. a matrix comprising one column consisting of m elements which describe the magnetic flux density at the m measuring points at the selected instant. n is a matrix of the same type which represents the noise components of the magnetic flux density at the individual measuring points. j is also a column matrix comprising 2s elements, each of which represents the two (mutually perpendicular) tangential components of the current density at the s voxels on the marked surface 3.

A is the Biot-Savart matrix of the type (m, 2s) whose matrix elements are defined by the geometrical relationships between the measuring points and the voxels; the matrix elements are thus unambiguously defined by the geometrical position of the associated measuring points and voxels.

For the above matrix equations to be solved unambiguously it is necessary that the matrix A has the rank n and that n=2s. In this case the desired matrix can be determined for j directly by inverting the matrix A. In the other cases, and also in the described case, an optimum estimate of the current density matrix j can be made by means of the so-called Moore-Penrose pseudo inverse functions. This method and its use for the reconstruction of the current density distribution is known inter alia from the article by Dallas et al "Bioelectric current image reconstruction from measurement of the generated magnetic fields" in "Medical Imaging", R. H. Schneider, S. J. Dwyer III. Editors, Proc. SPIE 767, pp. 2–10, 1987. Because the reconstruction is limited to the surfaces of volume elements $V_i$ specified by the unit 10 in the present case, this reconstruction is substantially more adequate than in the applications described in the cited publication where the current density distribution is reconstructed at all voxels on the basis of an estimate.

The result of the reconstruction process, therefore is the current density j or its mutually perpendicular tangential components at the voxels specified via the unit 10. This distribution can be displayed on a suitable display apparatus 12; in order to facilitate orientation, a tomogram which allows for recognition of the morphological structures on which the currents determined flow can be superposed on the image.

What is claimed is:

1. A device for reconstructing spatial current distributions in a biological object within which object volume elements exhibit current distributions produced by current sources in said object, it being presumed that said current sources are present on surfaces inside of the morphological structure of the object, said device comprising:

means for specifying a representation which contains the morphological structure of said object at said surfaces on which the current sources are presumed present;

means for measuring at a plurality of points outside the object the values of at least one component of the magnetic fields produced by respective ones of said current sources within the object manifesting said surfaces; and means for reconstructing the current distribution of the volume elements which are situated on said surfaces on the basis of said measured values.

2. A device for reconstructing the spatial current distribution in a biological object having a morphological structure within which object volume elements exhibit current distributions produced by current sources in said object, it being presumed that said current sources are present on specified surfaces inside of the morphological structure of the object, said device comprising:

measuring means for determining values of magnetic flux density produced by said presumed current sources outside said object;

memory means for storing said determined flux density values;

means for determining the volume location of the elements which are on specified surfaces inside said object; and reconstruction means for determining the current distributions at said determined volume elements from said stored values.

* * * * *